United States Patent
Schonbeck et al.

[11] 3,953,445
[45] *Apr. 27, 1976

[54] 3-PHENYL-6-HALO-PYRIDAZINYL THIO-AND DITHIO-CARBONATES

[75] Inventors: Rupert Schonbeck, Leonding near Linz; Engelbert Kloimstein, Eferding; Alfred Diskus; Engelbert Auer, both of Linz; Hubert Mayr, Leonding near Linz, all of Austria

[73] Assignee: Chemie Linz Aktiengesellschaft, Linz, Austria

[ * ] Notice: The portion of the term of this patent subsequent to Jan. 13, 1993, has been disclaimed.

[22] Filed: June 17, 1974

[21] Appl. No.: 480,309

[30] Foreign Application Priority Data
June 20, 1973 Germany............................ 2331398

[52] U.S. Cl.................................. 260/250 A; 71/92
[51] Int. Cl.².............. C07D 237/14; C07D 237/16
[58] Field of Search................................. 260/250 A

[56] References Cited
UNITED STATES PATENTS
3,790,571  2/1974  Diskus et al...................... 260/250 A FOREIGN PATENTS OR APPLICATIONS
2,256,172  5/1974  Germany Primary Examiner—Alton D. Rollins
Assistant Examiner—Diana G. Rivers
Attorney, Agent, or Firm—Wenderoth, Lind & Ponack

[57] ABSTRACT

Phenylpyridazines of the general formula:

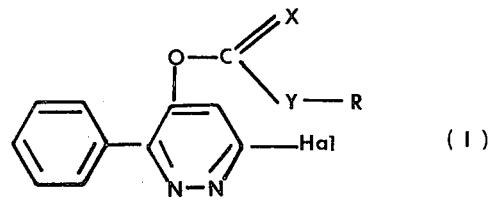

in which Hal is a chlorine or bromine atom, R is a straight-chain or branched alkyl group containing 1 to 18 carbon atoms or a phenyl group, and X and Y separately are oxygen or sulphur, but not both oxygen, a process for their preparation and herbicidal compositions containing them.

20 Claims, No Drawings

3-PHENYL-6-HALO-PYRIDAZINYL THIO-AND DITHIO-CARBONATES

This invention relates to phenylpyridazine compounds, a process for their preparation and their use as agents for combating weeds.

It has been known for some time that pyridazine derivatives influence the growth of plants. Thus pyridazines containing two or three halogen atoms or up to two halogen atoms and, in addition, alkylated amino groups, alkoxy groups or alkylmercapto groups are described in Austrian Pat. No. 198,997 as agents for influencing the growth of plants. The compounds which are described in detail in this prior Specification are either total herbicides or produce other effects on plants, such as, for example, leaf-fall.

In U.S. Pat. No. 3,010.962 3-chloro-pyridazine-6-oxyacetic acid is suitable as a hormonally acting agent for combating weeds, which does not, however, have a very broad spectrum of action.

U.S. Pat. No. 3,790.571, Diskus et al. discloses that 6-halo-4-hydroxy-3-phenylpyridazines have very good herbicidal properties, coupled with good toleration by useful plants, for example cereals.

It has now been found that hitherto unknown phenylpyridazines of the general formula (I) herein have even more advantageous herbicidal properties and also display good toleration by many useful plants, for example, cereals.

Accordingly the present invention provides a phenylpyridazine having the general formula:

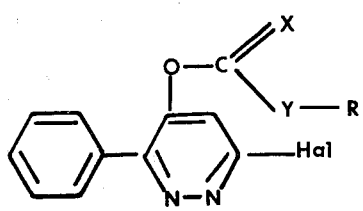

(I)

in which Hal is a chlorine or bromine atom, R is a straight-chain or branched alkyl group containing 1 to 18 carbon atoms or a phenyl group, and X and Y separately are oxygen or sulphur, but not both oxygen.

The compounds according to the invention are above all much more strongly active than the known 6-halo-4-hydroxy-3-phenylpyridazines, so that the quantity to be applied may be considerably reduced.

There are, of course, considerable differences in respect of toleration amongst the plants which are to be classed among the grasses. While cereals, maize and rice are found to be tolerant to the compounds according to the invention in applied quantities which suffice to kill off the weeds, the wild millet representatives (*Echinochloa crus galli* or cock's foot, *Setaria viridis* or green mat-grass, *Digitaria filiformis* or finger grass) are classed with the sensitive Graminae so that it is possible to combat these harmful grasses selectively by means of the compounds according to the invention. The best success in combating weeds is achieved when using the compounds in the young stage in the development of the plants (2 to 4 leaf stage of the wild millets).

Those compounds of formula (I) are particularly preferred in which one of X and Y is sulphur and the other is oxygen, the action of compounds in which Y is sulphur and X is oxygen being of equal rank with the action of those of the thiono compounds in which Y is oxygen and X is sulphur. The group R, preferably may be a straight-chain or branched alkyl group containing 2 to 12 carbon atoms, for example the ethyl, propyl, n-butyl, isobutyl, n-pentyl or n-hexyl group, straight-chain or branched octyl groups, n-decyl groups and n-dodecyl groups being particularly worthy of mention. Compounds of the formula (I) in which the group R has more than 12 carbon atoms, have a somewhat weaker action compared with compounds of the formula (I) with groups R of 2 to 12 carbon atoms, the optimum in respect of strength of action and toleration by crop plants probably being represented by compounds with groups R of 5 to 10 carbon atoms.

The invention also provides a process for the preparation of a phenylpyridazine of the general formula (I) which comprises reacting a phenylpyridazine of the general formula:

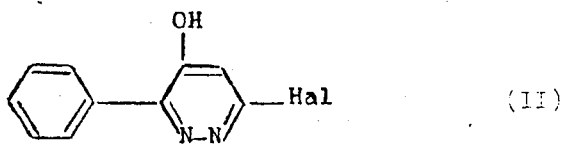

(II)

in which Hal is as defined in formula (I), or a salt thereof, if appropriate in the presence of a solvent and if appropriate with the addition of an acid acceptor, with an acid chloride of the general formula:

(III)

in which X, Y and R are as defined above.

Organic solvents, particularly inert aromatic hydrocarbons, may be employed in this process.

Preferably, it is possible to employ a salt of the abovementioned hydroxypyridazine with a tertiary amine in the reaction, an additional acid acceptor then being superfluous. The reaction is preferably conducted at ambient or slightly elevated temperature, but higher temperatures are not excluded.

It is generally advantageous to carry out the reaction in the absence of compounds containing hydroxyl groups, such as alcohols or water.

The compounds obtained in accordance with the invention are mostly liquids or solids of low melting point.

3-Phenyl-4-hydroxy-6-chloropyridazine, melting point 220°C. (decomposition), which is used as the starting material, may be obtained from 3-phenyl-4,6-dichloropyridazine by heating with sodium hydroxide solution.

Equally, 3-phenyl-4-hydroxy-6-bromopyridazine, melting point 215°C. (decomposition), is obtainable by reacting 3-phenyl-4,6-dibromopyridazine with sodium hydroxide solution at boiling point.

The esters of formula (I) according to the invention are mostly viscous liquids with a high boiling point, which cannot be distilled without decomposition.

The invention further provides a herbicidal composition for selectively combating weeds in cultivated areas, which comprises, as the active ingredient, one or more compounds of the general formula (I) in admixture with solid and/or liquid, inert extenders or diluents, emulsifiers and/or wetting agents.

Since the compounds of this invention are not active in the sense of growth substances, the danger of damaging neighbouring crops is substantially reduced. They are therefore also preferentially suitable for combating weeds in crop plantations in the immediate vicinity of crops which are sensitive to growth substances.

The compositions according to the invention may be prepared in the form of dispersions of emulsions, as pulverulent preparations or in the form of granules. It is also possible to admix them with other herbicidal active substances.

The following substances are particularly suitable: the salts and esters of 2,4-dichlorophenoxyacetic acid (2,4-D), 2-methyl-4-chlorophenoxyacetic acid (MCPA), 2,4,5-trichlorophenoxyacetic acid (2,4,5-T), 2-(4-chloro-2-methylphenoxy)-propionic acid (CMPP), 2-(2,4-dichlorophenoxy)-propionic acid (2,4-DP), 4-(2,4-dichlorophenoxy)-butyric acid (2,4-DB), 4-(4-chloro-2-methylphenoxy)-butyric acid (MCPB), 2-(2,4,5-trichlorophenoxy)-propionic acid (2,4,5-TP) and 4-chloro-2-oxobenzothiazolin-3-yla-cetic acid (Benazolin), and also herbicidally active benzoic acid derivatives, such as, for example, 3,6-dichloro-2-methoxybenzoic acid (Dicamba) or 2,5-dichloro-3-aminobenzoic acid (Amiben). Further favourable effects are also achieved by admixing the compounds according to the invention with urea derivatives, such as, for example, N-(3,4-dichlorophenyl)-N'-methoxy-N'-methylurea, N-(2-benzthiazolyl)-N-methyl-N'-methylurea, 3-(3-chloro-p-tolyl)-1,1-dimethylurea, and N-(3-chloro-4-methoxyphenyl)-N',N'-dimethylurea, and/or with derivatives of 1,3,5-triazine, such as, for example, 2-chloro-4,6-diethylamino-1,3,5-triazine, 2-chloro-4-ethylamino-6-isopropylamino-1,3,5-triazine or 2-methylmercapto-4-(3-methoxypropylamino)-6-isopropylamino-1,3,5-triazine.

Mixtures with 2-sec.-butyl4,6-dinitrophenylacetate, 3,5-diiodo-4-hydroxybenzonitrile, 3,5-dibromo-4-hydroxybenzonitrile, 3,5-dibromo-4-hydroxybenzaldoxime-O-(2',4'dinitrophenyl) ether, 3-isopropyl-2,1,3-benzo-thiadiazinone-(4)-2,2-dioxide are also advantageous, equally mixtures with acid anilides, such as, for example, 3,4-dichloropropionanilide, and derivatives of thiolcarbamic acid, such as, for example, S-ethyl-NN-hexamethylene-thiol carbamate. The possibility of mixtures with various growth regulators, such as, for example, 2-chloro-ethyltrimethylammonium chloride (Chlormequat) is also found to be of great practical importance. Applying the compounds according to the invention conjointly with fungicides, insecticides, other biocides and/or plant nutrients is also advantageous.

For compositions in the form of aqueous dispersions or emulsions, it is advisable to add a dispersing agent such as, for example, sodium olely-methyl-tauride or salts of ligninsulphonic acid. It is also very advantageous to apply the compositions according to the invention in the form of wettable powders. In this case it is advisable to adsorb the active compound in a material of strong adsorbent power, such as, for example, highly dispersed silica or kieselguhr. This concentrate of active compound may be dispersed in water after being treated wih dispersing agents and inorganic extenders. It has been found appropriate to add surface-active agents, for example sulphonic acids. Suitable solid extenders are, inter alia, various kinds of clay, for example kaolin, or silicic acid, kieselguhr or mineral silica.

It is advantageous to combine the compounds according to the invention with a non-phytotoxic oil, for example a mineral oil-emulsifier mixture, consisting of a paraffinic mineral oil and an emulsifier. The herbicidal action may be increased further by the addition of such a "spray-oil" to a spray solution of the compounds according to the invention. Such combinations customarily contain 0.1 to 10 kg. of the active compound according to the present invention and 1 to 10 liters of a non-phytotoxic oil, dispersed in a quantity of 50 to 1,000 liters of water.

the quantity to be applied is as a rule between 0.2 and 5 kg/hectare, preferably 0.5 to 2 kg/hectare, based upon the compound of formula (I). When admixed with other herbicidal active substances, the quantity of active compound to be applied may be reduced further, preferably to 0.2 to 1 kg/hectare.

The preparation and the mode of operation of the compounds and compositions according to the invention are illustrated in the following Examples:

EXAMPLE 1

1.5 parts of 3-phenyl-4-hydroxy-6-chloropyridazine were suspended in 8 parts of benzene and stirred for 20 minutes with 0.75 part of triethylamine and a solution of 1.08 parts of chlorothioformic acid S-n-butyl ester in 2 parts of benzene was added rapidly to the heterogeneous liquid mixture. In the course thereof the temperature of the mixture rose, during 2 minutes, from 22°C to 45°C and fine crystals of triethylamine hydrochloride were formed. After a reaction period of two hours, 3 parts of water were added, the mixture was stirred for 10 minutes and the aqueous phase was removed and the remainder was again stirred thoroughly with 1 part of water.

The benzene solution was dried with 0.5 part of $Na_2SO_4$, and filtered off and the filtrate was evaporated in vacuo.

2.30 parts of a brown oily product were obtained, corresponding to a 98% yield of O-[3-phenyl-6-chloropyridazinyl-(4)]-S-(n-butyl)-thiocarbonate, $n_D20$ = 1.5896. C calculated 55.81%; H calculated 4.68%; N calculated 8.68%; Cl calculated 10.98%; S calculated 9.93%. C found 55.5%; H found 4.7%; N found 8.6%; Cl found 11.3%; S found 10.1%.

3-Phenyl-4-hydroxy-6-chloropyridazine and 3-phenyl-4-hydroxy-6-bromopyridazine were reacted with the corresponding chlorothioformic acid esters according to the procedure described in Example 1 and the following compounds were obtained:

O-(3-Phenyl-6-chloropyridazinyl-(4))-S-(n-propyl)-thiocarbonate: 70% Yield: $n_D20$ = 1.5964. C calculated 54.55%, H calculated 4.24%; N calculated 9.07%; Cl calculated 11.48%; S calculated 10.36%. C found 54.3%; H found 4.6%; N found 8.9%; Cl found 11.9%; S found 10.8%.

O-(3-Phenyl-6-bromopyridazinyl-(4))-S-(n-butyl)-thiocarbonate: 51% Yield: $n_D20$ = 1.6033. C calculated 49.05%; H calculated 4.12%; N calculated 7.63%; Br calculated 21.76%; S calculated 8.73%. C found 50.0%; H found 4.7%; N found 7.4%; Br found 20.7%; S found 9.4%.

O-(3-Phenyl-6-chloropyridazinyl-(4))-S-(butyl-(2'))-thiocarbonate: 71.5% Yield: $N_D20$ = 1.5897. C calculated 55.81%; H calculated 4.68%; N calculated 8.68%; Cl calculated 10.98%; S calculated 9.93%. C found 55.6%; H found 5.1%; N found 8.6%; Cl found 11.5%; S found 11.0%.

O-(3-Phenyl-6-chloropyridazinyl-(4))-S-(n-pentyl)-thiocarbonate: 72.5% Yield: $n_D20 = 1.5834$. C calculated 57.05%; H calculated 5.09%; N calculated 8.32%; Cl calculated 10.53%; S calculated 9.52%. C found 57.1%; H found 5.5%; N found 8.0%; Cl found 11.3%; S found 10.1%.

O-(3-Phenyl-6-chloropyridazinyl-(4))-S-(3'-methyl-butyl-(1'))-thiocarbonate: 79% Yield: $n_D20 = 1.5790$. C calculated 57.05%; H calculated 5.09%; N calculated 8.32%; Cl calculated 10.53%; S calculated 9.52%. C found 57.6%; H found 5.9%; N found 7.8%; Cl found 10.7%; S found 10.2%.

O-(3-Phenyl-6-chloropyridazinyl-(4))-S-(n-hexyl)-thiocarbonate: 71% Yield: $n_D20 = 1.5713$. C calculated 58.19%; H calculated 5.46%; N calculated 7.99%; Cl calculated 10.11%; S calculated 9.14%. C found 57.9%; H found 6.3%; N found 7.9%; Cl found 10.5%; S found 9.9%.

O-(3-Phenyl-6-chloropyridazinyl-(4))-S-(n-heptyl)-thiocarbonate: 85% Yield: $n_D20 = 1.5660$. C calculated 59.25%; H calculated 5.80%; N calculated 7.68%; Cl calculated 9.72%; S calculated 8.79%. C found 58.9%; H found 6.1%; N found 7.2%; Cl found 10.1%; S found 9.2%.

O-(3-Phenyl-6-chloropyridazinyl-(4))-S-(n-octyl)-thiocarbonate: 85% Yield: $n_D20 = 1.5689$. C calculated 60.22%; H calculated 6.12%; N calculated 7.39%; Cl calculated 9.39%; S calculated 8.41%. C found 60.3%; H found 6.3%; N found 7.1%; Cl found 9.1%; S found 8.7%.

O-(3-Phenyl-6-bromopyridazinyl-(4))-S-(n-octyl)-thiocarbonate: 87% Yield: $n_D20 = 1.5774$: C calculated 53.90%; H calculated 5.48%; N calculated 6.62%; Br calculated 18.88%; S calculated 7.57%. C found 55.0%; H found 5.8%; N found 6.3%; Br found 17.7%; S found 8.0%.

O-(3-Phenyl-6-chloropyridazinyl-(4))-S-(n-dodecyl)-thiocarbonate 76% Yield: $n_D20 = 1.5498$. C calculated 63.5%; H calculated 7.18%; N calculated 6.44%; Cl calculated 8.15%; S calculated 7.37%. C found 63.2%; H found 8.0%; N found 6.2%; Cl found 8.6%; S found 7.5%.

O-(3-Phenyl-6-chloropyridazinyl-(4))-S-(phenyl)-thiocarbonate: 63% Yield: $n_D20 = 1.6442$. C calculated 59.56%; H calculated 3.23%; N calculated 8.17%; Cl calculated 10.34%; S calculated 9.35%. C found 61.2%; H found 4.0%; N found 7.4%; Cl found 9.8%; S found 9.8%.

O-[3-Phenyl-6-chloropyridazinyl-(4)]-S-(n-decyl)-thiocarbonate: 79.6% Yield: $n_D20 = 1.5600$. calculated: C, 61.97%; H, 6.70%; N, 6.88%; Cl, 8.71%; S, 7.88%; found: C, 62.0%; H, 6.9%; N, 6.9%; Cl, 8.8%; S 7.5%.

O-[3-Phenyl-6-chloropyridazinyl-(4)]-S-(2-ethyl-n-hexyl)-thiocarbonate: 64% Yield: $n_D20 = 1.5735$. calculated: C, 60.22%; H, 6.12%; N, 7.39%; Cl, 9.36%; S, 8.46%; found: C, 61.0%; H, 6.7%; N, 7.2%; Cl, 9.5%; S, 9.0%.

O-[3-Phenyl-6-chloropyridazinyl-(4)]-S-(2ethyl-4-methylpentyl)-thiocarbonate: 69% Yield: $n_D20 = 1.5715$. calculated: C, 60.22%; H, 6.12%; N, 7.39%; Cl, 9.36%; S, 8.46%; found: C, 60.2%; H, 6.3%; N, 7.3%; Cl, 9.1%; S, 8.6%.

EXAMPLE 2

10 parts of 3-phenyl-4-hydroxy-6-chloropyridazine were suspended in 100 parts of benzene and 5.2 parts of triethylamine were added and the mixture was stirred for 10 minutes; a solution of 5.7 parts of chlorothionoformic acid O-ethyl ester in 20 parts of benzene was then added and the mixture allowed to react for 20 minutes. 20 parts of water were then added, the mixture was stirred for 5 minutes and the aqueous phase was removed; the benzene layer was washed with water, dried with $Na_2SO_4$, filtered and evaporated in vacuo and the product recrystallised from petroleum ether. 8.7 parts of a white product were obtained, corresponding to 61% yield of O-(3-phenyl-6-chloropyridazinyl-(4))-O-(ethyl)-thionocarbonate. Melting point = 77° - 79°C. C calculated 52.97%; H calculated 3.76%; N calculated 9.51%; Cl calculated 12.03%; S calculated 10.88%. C found 52.5%; H found 3.7%; N found 9.3%; Cl found 11.9%; S found 11.1%.

The following compounds were obtained analogously.

O-(3-Phenyl-6-chloropyridazinyl-(4))-O-(n-propyl)-thionocarbonate: 53% Yield: Melting point = 58° - 61°C. C calculated 54.45%; H calculated 4.24%; N calculated 9.07%; Cl calculated 11.48%; S calculated 10.38% C found 54.5%; H found 4.3%; N found 9.3%; Cl found 11.5%; S found 10.5%.

O-(3-Phenyl-6-chloropyridazinyl-(4))-O-(n-butyl)-thionocarbonate: 57% Yield: $N_D20 = 1.5824$: C calculated 55.81%; H calculated 4.68%; N calculated 8.68%; Cl calculated 10.98%; S calculated 9.93%. C found 55.1%; H found 4.7%; N found 7.9%; Cl found 11.3%; S found 10.2%.

O-(3-Phenyl-6-chloropyridazinyl-(4))-O-(isobutyl)-thionocarbonate: 64% Yield: $n_D20 = 1.5752$. C calculated 55.81%; H calculated 4.68%; N calculated 8.68%; Cl calculated 10.98%; S calculated 9.93%. C found 55.0%; H found 5.1%; N found 8.3%; Cl found 11.0%; S found 10.0%.

O-(3-Phenyl-6-bromopyridazinyl-(4))-O-(isobutyl)-thionocarbonate: 45% Yield: $n_D20 = 1.5838$. C calculated 49.05%; H calculated 4.12%; N calculated 7.63%; Br calculated 21.76%; S calculated 8.73%. C found 48.7%; H found 4.4%; N found 7.2%; Br found 22.1% S found 9.0%.

O-(3-Phenyl-6-chloropyridazinyl-(4))-O-(n-hexyl)-thionocarbonate: 72% Yield: $n_D20 = 1.5605$. C calculated 58.19%; H calculated 5.46%; N calculated 7.99%; Cl calculated 10.11%; S calculated 9.14%. C found 58.1%; H found 6.1%; N found 7.8%; Cl found 10.1%; S found 9.3%.

EXAMPLE 3

10 parts of 3-phenyl-4-hydroxy-6-chloropyridazine were suspended in 100 parts of benzene, 5.0 parts of triethylamine were added and the mixture was stirred for 20 minutes; a solution consisting of 9.0 parts of chlorodithioformic acid phenyl ester in 20 parts of benzene was then added, the mixture allowed to react for 1 hour, the triethylamine hydrochloride was then dissolved out by means of 20 parts of water and the benzene solution was dried with $Na_2SO_4$, filtered and evaporated. The residue was dissolved in petroleum ether and the solution was filtered with the aid of charcoal and once more evaporated.

13.5 parts of a red, highly viscous oil were obtained, corresponding to a 78% yield of O-[3-phenyl-6- chloropyridazinyl(4)]-S-(phenyl)-dithiocarbonate. C calculated 56.89%; H calculated 3.09%; N calculated 7.81%; Cl calculated 9.88%; S calculated 17.87%. C found 56.5%; H found 3.4%; N found 7.2%; Cl found 10.2%; S found 18.1%.

EXAMPLE 4

20 parts of 3-phenyl-4-hydroxy-6-chloropyridazine were suspended in 180 parts of benzene. 9 parts of pyridine were added, the mixture was stirred for 10 minutes and 14 parts of chlorothioformic acid S-n-butyl ester were added to the suspension, which was stirred for 1 hour. It was then shaken for 1 minute with 50 parts of water, the aqueous phase was removed and the benzene solution was dried and evaporated. 28 parts of a yellow oil were obtained, corresponding to an 89% yield of O-(3-phenyl-6-chloropyridazinyl-(4))-S-(n-butyl)-thiocarbonate. $n_D 20 = 1.5896$.

EXAMPLE 5

20 parts of O-(3-phenyl-6-chloropyridazinyl-(4))-S-(n-butyl)-thiocarbonate, 70 parts of xylene and 10 parts of alkylarylsulphonate, mixed with polyoxyethylene-sorbitane-tall oil ester, were mixed. A stable emulsion was obtained by stirring the emulsion concentrate into the quantity of water required for application to the plant.

EXAMPLE 6

50 parts of O-(3-phenyl-6-chloropyridazinyl-(4))-S-(n-butyl)-thiocarbonate, 43 parts of xylene and 7 parts of alkylarylsulphonate, mixed with polyoxyethylene-sorbitane-tall oil ester, were mixed. A stable emulsion was obtained by stirring the emulsion concentrate into water. All the other agents according to the invention were formulated in a similar manner.

EXAMPLE 7

250 parts of O-[3-phenyl-6-chloropyridazinyl-(4)]-S-(n-octyl)-thiocarbonate were absorbed by mixing with 134.6 parts of highly disperse silica. 381.3 parts of the magnesium salt of methylchlorophenoxypropionic acid, 70 parts of the sodium salt of ligninsulphonic acid, 20 parts of the sodium salt of diisobutylnaphthalenesulphonic acid, 10 parts of the sodium salt of oleic acid methyltauride and 134.1 parts of mineral silica were added to this pre-concentrate and the mixture was ground. This wettable powder was dispersed in water before use.

EXAMPLE 8

211 parts of the monomethylamine salt of 2,4-dichlorophenoxyacetic acid, 70 parts of the sodium salt of ligninsulphonic acid, 20 parts of the sodium salt of diisobutylnaphthalenesulphonic acid, 10 parts of the sodium salt of oleic acid methyltauride and 304.4 parts of mineral silica were added to a preconcentrate prepared from 250 parts of O-[3-phenyl-6-chloropyridazinyl-(4)]-S-(n-octyl)-thiocarbonate and 134.6 parts of highly disperse silica and the mixture was ground. The wettable powder thus obtained was dispersed in water before use.

EXAMPLE 9

A pre-concentrate obtained by mixing 500 parts of O-[3-phenyl-6-chloropyridazinyl-(4)]-S-(n-octyl)-thiocarbonate with 269.2 parts of highly disperse silica was mixed with 70 parts of the sodium salt of ligninsulphonic acid, 20 parts of the sodium salt of diisobutylnaphthalenesulphonic acid, 10 parts of the sodium salt of oleic acid methyltauride and 130.8 parts of mineral silica and the mixture was ground. This wettable powder was dispersed in water before use.

EXAMPLE 10

400 parts of O-[3-phenyl-6-chloropyridazinyl-(4)]-S-(n-octyl)-thiocarbonate were mixed wih 215.3 parts of highly disperse silica and 66.2 parts of the potassium salt of 2-methoxy-3,6-dichlorobenzoic acid, 70 parts of the sodium salt of ligninsulphonic acid, 20 parts of the sodium salt of diisobutylnaphthalenesulphonic acid, 10 parts of the sodium salt of oleic acid methyltauride and 218.5 parts of mineral silica were added to this pre-concentrate. The mixture was then ground. The wettable powder thus prepared gives a stable suspension on being stirred into water.

EXAMPLE 11

The following weeds, grown in the greenhouse,

| | |
|---|---|
| Erodium cicutarium | Stork's bill |
| Centaurea jacea | Knapweed |
| Lapsana communis | Nipplewort |
| Galium aparine | Cleavers |
| Stellaria media | Chickweed |
| Matricaria chamomilla | Camomile |
| Lamium purpureum | Dead nettle |
| Veronica hederaefolia | Speedwell | were sprayed, after the weeds had reached the 4–6 leaf stage, with the spraying solution of the agents according to the invention, such as are described in Examples 5, 6 and 9.

The spraying solution was prepared by diluting an emulsion concentrate with water. The application of active substance was in each case 300 g. and 600 g. of the active compound per hectare. The herbicidal effect on the weeds was determined 14 days after treatment according to the European Weed Research Council rating scheme.

The numerical values 1 to 9 correspond to the following degrees of destruction:

| Rating of the herbicidal action | corresponding to % destruction of the weeds |
|---|---|
| 1 | 100 |
| 2 | 97.5 |
| 3 | 95 |
| 4 | 90 |
| 5 | 85 |
| 6 | 75 |
| 7 | 65 |
| 8 | 32.5 |
| 9 | 0 |

| Name | Active substance kg/hectare | Erodium circu- tarium | Cen- taurea jacea | Lapsana com- munis | Galium aparine | Stel- laria media | Matri- caria chamo- milla | Lamium purpureum | Veronica hederae- folia |
|---|---|---|---|---|---|---|---|---|---|
| | Herbicidal action on various weeds (Ratings 1 – 9) | | | | | | | | |
| O-(Ph-Cl)-S-(n-propyl)-thiocarbonate | 0.3  0.6 | 1/1 | 1/1 | 1/1 | 1/1 | 4/1 | 1/1 | 1/1 | 1/1 |
| O-(Ph-Cl)-S-(n-butyl)-thiocarbonate | | 1/1 | 1/1 | 1/1 | 1/1 | 3/1 | 1/1 | 1/1 | 1/1 |
| O-(Ph-Br)-S-n(butyl)-thiocarbonate | | 1/1 | 1/1 | 1/1 | 1/1 | 4/1 | 1/1 | 1/1 | 1/1 |
| O-(Ph-Cl)-S-[butyl-(2′)]-thiocarbonate | | 1/1 | 1/1 | 1/1 | 1/1 | 4/1 | 1/1 | 1/1 | 1/1 |
| O-(Ph-Cl)-S-(n-pentyl)-thiocarbonate | | 1/1 | 1/1 | 1/1 | 1/1 | 5/1 | 1/1 | 1/1 | 1/1 |
| O-(Ph-Cl)-S-[3′-methyl-butyl-(1′)]-thiocarbonate | | 1/1 | 1/1 | 1/1 | 1/1 | 5/1 | 1/1 | 1/1 | 1/1 |
| O-(Ph-Cl)-S-(n-hexyl)-thiocarbonate | | 1/1 | 1/1 | 1/1 | 1/1 | 5/1 | 1/1 | 1/1 | 1/1 |
| O-(Ph-Cl)-S-(n-heptyl)-thiocarbonate | | 1/1 | 1/1 | 1/1 | 1/1 | 5/1 | 1/1 | 1/1 | 1/1 |
| O-(Ph-Cl)-S-(n-octyl)-thiocarbonate | | 1/1 | 1/1 | 1/1 | 1/1 | 5/1 | 1/1 | 1/1 | 1/1 |
| O-(Ph-Br)-S-(n-octyl)-thiocarbonate | | 1/1 | 1/1 | 1/1 | 1/1 | 5/1 | 1/1 | 1/1 | 1/1 |
| O-(Ph-Cl)-S-(n-dodecyl)-thiocarbonate | | 1/1 | 1/1 | 2/1 | 3/2 | 5/3 | 2/1 | 3/1 | 3/2 |
| O-(Ph-Cl)-S-(phenyl)-thiocarbonate | | 1/1 | 1/1 | 4/2 | 5/3 | 6/4 | 2/1 | 3/1 | 4/2 |
| O-(Ph-Cl)-O-(ethyl)-thionocarbonate | | 1/1 | 1/1 | 1/1 | 1/1 | 3/1 | 1/1 | 1/1 | 1/1 |
| O-(Ph-Cl)-O-(n-propyl)-thionocarbonate | | 1/1 | 1/1 | 1/1 | 1/1 | 3/1 | 1/1 | 1/1 | 1/1 |
| O-(Ph-Cl)-O-(n-butyl)-thionocarbonate | | 1/1 | 1/1 | 1/1 | 1/1 | 3/1 | 1/1 | 1/1 | 1/1 |
| O-(Ph-Cl)-O-(isobutyl)-thionocarbonate | | 1/1 | 1/1 | 1/1 | 1/1 | 3/1 | 1/1 | 1/1 | 1/1 |
| O-(Ph-Br)-O-(isobutyl)-thionocarbonate | | 1/1 | 1/1 | 1/1 | 1/1 | 3/1 | 1/1 | 1/1 | 1/1 |
| O-(Ph-Cl)-O-(n-hexyl)-thionocarbonate | | 1/1 | 1/1 | 1/1 | 1/1 | 3/1 | 1/1 | 1/1 | 1/1 |
| O-(Ph-Cl)-S-(phenyl)-di-thiocarbonate | | 1/1 | 6/3 | 4/2 | 5/3 | 6/5 | 2/1 | 3/2 | 4/2 |

O-(Ph-Cl) = O-(3-phenyl-6-chloropyridazinyl-4)-
O-(Ph-Br) = O-(3-phenyl-6-bromopyridazinyl-4)-

As can be seen from Example 7, in the case of nearly all the compounds according to the invention, even 600 g of the active compound per hectare are sufficient for complete destruction of the weeds. Even with only 300 g of active compound per hectare, an excellent herbicidal effect can still be achieved in the case of the majority of the weeds.

EXAMPLE 12

The following wild millets were grown in a greenhouse:

*Echinocholoa crus galli*    cock's foot
*Setaria viridis*    green mat-grass
*Digitaria filiformis*    finger grass After reaching the 4-leaf stage, the millet plants were sprayed with spraying solutions of the compounds according to the invention, such as are described in Examples 5, 6 or 9. The herbicidal effect on the wild millets was determined, 14 days after the application of the agents, according to the assessment scheme mentioned in Example 7. In each case the dosage corresponded to 1.0 and 1.5 kg of the active compound per hectare.

| Active Substance No. | Herbicidal action on wild millets (Ratings 1 - 9) | | | |
|---|---|---|---|---|
| | Active substance kg/hectare | Echinochloa crus galli (cock's foot) | Setaria viridis (green mat grass) | Digitaria filiformis (finger grass) |
| O-(Ph-Cl)-S-(n-propyl)-thiocarbonate | 1.0  1.5 | 4/2 | 4/2 | 5/2 |
| O-(Ph-Cl)-S-(n-butyl)-thiocarbonate | | 4/1 | 5/1 | 5/2 |
| O-(Ph-Br)-S-(n-butyl)-thiocarbonate | | 5/2 | 4/2 | 5/2 |
| O-(Ph-Cl)-S-(butyl-(2))-thiocarbonate | | 4/1 | 5/1 | 5/1 |
| O-(Ph-Cl)-S-(n-pentyl)-thiocarbonate | | 4/1 | 5/1 | 5/2 |
| O-(Ph-Cl)-S-(3'-methylbutyl-(1'))-thiocarbonate | | 4/1 | 4/1 | 4/1 |
| O-(Ph-Cl)-S-(n-hexyl)-thiocarbonate | | 4/2 | 5/2 | 5/2 |
| O-(Ph-Cl)-S-(n-heptyl)-thiocarbonate | | 4/1 | 5/2 | 5/2 |
| O-(Ph-Cl)-S-(n-octyl)-thiocarbonate | | 4/2 | 5/3 | 5/3 |
| O-(Ph-Br)-S-(n-octyl)-thiocarbonate | | 5/3 | 5/3 | 5/3 |
| O-(Ph-Cl)-S-(n-dodecyl)-thiocarbonate | | 3/1 | 3/1 | 4/1 |
| O-(Ph-Cl)-S-(phenyl)-thiocarbonate | | 4/1 | 3/1 | 4/2 |
| O-(Ph-Cl)-O-(ethyl)-thionocarbonate | | 5/2 | 3/1 | 5/2 |
| O-(Ph-Cl)-O-(n-propyl)-thionocarbonate | | 4/1 | 4/1 | 5/2 |
| O-(Ph-Cl)-O-(n-butyl)-thionocarbonate | | 3/1 | 3/1 | 4/1 |
| O-(Ph-Cl)-O-(isobutyl)-thionocarbonate | | 5/2 | 5/2 | 5/2 |
| O-(Ph-Br)-O-(isobutyl)-thionocarbonate | | 4/1 | 4/1 | 5/2 |
| O-(Ph-Cl)-O-(n-hexyl)-thionocarbonate | | 5/2 | 5/2 | 5/2 |
| O-(Ph-Cl)-S-(phenyl)-dithiocarbonate | | 5/2 | 5/2 | 5/2 |

O-(Ph-Cl) = O-(3-phenyl-6-chloropyridazinyl-(4))-
O-(Ph-Br) = O-(3-phenyl-6-bromopyridazinyl-(4))-

EXAMPLE 13

The following useful plants, grown in a greenhouse:

| | | |
|---|---|---|
| Triticum vulgare | Wheat | |
| Hordeum sativum | Barley | |
| Avena sativa | Oats | |
| Secale cereale | Rye | |
| Zea mays | Maize | |
| Spinacia oleracea | Spinach | |
| Vicia faba | Horse bean | |
| Beta vulgaris | Sugar beet | |
| Raphanus sativus var.radicula | Radish | |

| Rating of damage to the useful plants | Corresponding to % thinning out or scorching or inhibition of growth |
|---|---|
| 1 | 0 |
| 2 | 2.5 |
| 3 | 5 |
| 4 | 10 |
| 5 | 15 |
| 6 | 25 |
| 7 | 35 |
| 8 | 67.5 |
| 9 | 100 | were sprayed with the emulsions of the compounds according to the invention described in Example 7. At the time of treatment, the cereals and the maize had developed 4 leaves; the sugar beet, the horse beans, the radish and the spinach had developed the cotyledons or the primary leaves and the first pair of foliage leaves.

The dosage corresponded to 0.6 and 1.0 kg of active substance per hectare.

The degree of damage to the useful plants was determined, 14 days after treatment, according to the following scheme:

As the example shows, amongst the useful plants the representatives of the Gramineae in particular display an extensive tolerance towards the compounds according to the invention, so that these substances are very suitable for selectively combating weeds in, for example, cereal cultivation.

If spray dispersions according to Example 9 are employed, the toleration by cultivated plants is even more advantageous.

| Cultivated plants - toleration (Ratings 1 - 9) | | | | | | | | | | |
|---|---|---|---|---|---|---|---|---|---|---|
| Name | Active substance kg/hectare | Triticum vulgare | Hordeum sativum | Avena sativa | Secale cereale | Zea mays | Spinacia oleracea | Vicia faba | Beta vulgaris | Raphanus sativus |
| O-(PH-Cl)-S-(n-propyl)-thiocarbonate | 0.6  1.0 | 1/1 | 1/1 | 1/1 | 1/1 | 1/1 | 6/8 | 3/4 | 9/9 | 3/7 |
| O-(Ph-Cl)-S-(n-butyl)-thiocarbonate | | 1/1 | 1/1 | 1/1 | 1/1 | 1/1 | 8/9 | 3/5 | 9/9 | 3/9 |
| O-(Ph-Br)-S-(n-butyl)-thiocarbonate | | 1/1 | 1/1 | 1/1 | 1/1 | 1/1 | 8/9 | 2/5 | 9/9 | 3/9 |
| O-(Ph-Cl)-S-(butyl-(2'))-thiocarbonate | | 1/1 | 1/1 | 1/1 | 1/1 | 1/1 | 7/9 | 3/6 | 9/9 | 3/9 |
| O-(Ph-Cl)-S-(n-pentyl)-thiocarbonate | | 1/1 | 1/1 | 1/1 | 1/1 | 1/1 | 7/9 | 2/5 | 9/9 | 3/9 |
| O-(Ph-Cl)-S-[(3')-methyl-butyl-(1')]-thiocarbonate | | 1/1 | 1/1 | 1/1 | 1/1 | 1/1 | 8/9 | 3/6 | 9/9 | 3/9 |
| O-(Ph-Cl)-S-(n-hexyl)-thiocarbonate | | 1/1 | 1/1 | 1/1 | 1/1 | 1/1 | 7/9 | 3/6 | 9/9 | 3/9 |
| O-(Ph-Cl)-S-(n-heptyl)-thiocarbonate | | 1/1 | 1/1 | 1/1 | 1/1 | 1/1 | 7/9 | 3/6 | 9/9 | 3/9 |
| O-(Ph-Cl)-S-(n-octyl)-thiocarbonate | | 1/1 | 1/1 | 1/1 | 1/1 | 1/1 | 7/9 | 3/5 | 9/9 | 3/9 |

-continued

| Name | Active substance kg/hectare | Cultivated plants - toleration (Ratings 1 - 9) | | | | | | | |
|---|---|---|---|---|---|---|---|---|---|
| | | Triticum vulgare | Hordeum sativum | Avena sativa | Secale cereale | Zea mays | Spinacia oleracea | Vicia faba | Beta vulgaris | Raphanus sativus |
| O-(Ph-Br)-S-(n-octyl)-thiocarbonate | 0.6  1.0 | 1/1 | 1/1 | 1/1 | 1/1 | 1/1 | 7/8 | 3/6 | 9/9 | 3/9 |
| O-(Ph-Cl)-S-(n-dodecyl)-thiocarbonate | | 1/1 | 1/1 | 1/1 | 1/1 | 1/1 | 5/6 | 2/5 | 7/9 | 2/8 |
| O-(Ph-Cl)-S-(phenyl)-thiocarbonate | | 1/1 | 1/1 | 1/1 | 1/1 | 1/1 | 5/6 | 2/5 | 7/9 | 2/7 |
| O-(Ph-Cl)-O-(ethyl)-thionocarbonate | | 1/1 | 1/1 | 1/1 | 1/1 | 1/1 | 7/8 | 3/6 | 9/9 | 3/9 |
| O-(Ph-Cl)-O-(n-propyl)-thionocarbonate | | 1/1 | 1/1 | 1/1 | 1/1 | 1/1 | 7/9 | 3/6 | 9/9 | 3/9 |
| O-(Ph-Cl)-O-(n-butyl)-thionocarbonate | | 1/1 | 1/1 | 1/1 | 1/1 | 1/1 | 7/9 | 4/6 | 9/9 | 3/9 |
| O-(Ph-Cl)-O-(isobutyl)-thionocarbonate | | 1/1 | 1/1 | 1/1 | 1/1 | 1/1 | 6/8 | 3/6 | 9/9 | 3/9 |
| O-(Ph-Br)-O-(isobutyl)-thionocarbonate | | 1/1 | 1/1 | 1/1 | 1/1 | 1/1 | 6/8 | 3/6 | 9/9 | 3/9 |
| O-(Ph-Cl)-O-(n-hexyl)-thionocarbonate | | 1/1 | 1/1 | 1/1 | 1/1 | 1/1 | 7/9 | 3/6 | 9/9 | 3/9 |
| O-(Ph-Cl)-S-(phenyl)-dithiocarbonate | | 1/1 | 1/1 | 1/1 | 1/1 | 1/1 | 4/6 | 2/5 | 7/9 | 2/7 |

O-(Ph-Cl) = O-(3-phenyl-6-chloropyridazinyl-4)-
O-(Ph-Br) = O-(3-phenyl-6-bromopyridazinyl-4)-

What we claim is:
1. A Phenylpyridazine having the formula:

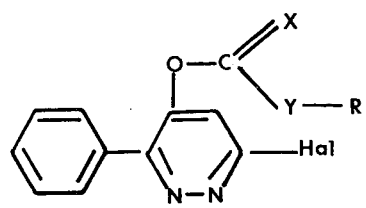

(I)

in which Hal is selected from the group consisting of chlorine or bromine, R is selected from the group consisting of straight chain alkyl and branched alkyl, both having up to 12 carbon atoms and phenyl, and X and Y are selected from the group consisting of oxygen and sulphur, whereby one of X and Y always is sulphur.

2. The compound according to claim 1, O-[3-Phenyl-6-chloropyridazinyl-(4)]-S-(n-propyl)-thiocarbonate.

3. The compound according to claim 1, O-3-Phenyl-6-chloropyridazinyl-(4)]-S-(n-butyl)-thiocarbonate.

4. The compound according to claim 1, O-[3-Phenyl-6-bromopyridazinyl-(4)]-S-(n-butyl)-thiocarbonate.

5. The compound according to claim 1, O-[3-Phenyl-6-chloropyridazinyl-(4)]-S-[butyl-(2')]-thiocarbonate.

6. The compound according to claim 1, O-[3-Phenyl-6-chloropyridazinyl-(4)]-S-(n-pentyl)-thiocarbonate.

7. The compound according to claim 1, O-[3-Phenyl-6-chloropyridazinyl-(4)]-S-[3'-methyl-butyl-(1')]-thiocarbonate.

8. The compound according to claim 1, O-[3-Phenyl-6-chloropyridazinyl-(4)]-S-(n-hexyl)-thiocarbonate.

9. The compound according to claim 1, O-[3-Phenyl-6-chloropyridazinyl-(4)]-S-(n-heptyl)-thiocarbonate.

10. The compound according to claim 1, O-[3-Phenyl-6-chloropyridazinyl-(4)]-S-(n-octyl)-thiocarbonate.

11. The compound according to claim 1, O-[3-Phenyl-6-bromopyridazinyl-(4)]-S-(n-octyl)-thiocarbonate.

12. The compound according to claim 1, O-[3-Phenyl-6-chloropyridazinyl-(4)]-S-(n-dodecyl)-thiocarbonate.

13. The compound according to claim 1, O-[3-Phenyl-6-chloropyridazinyl-(4)]-S-(phenyl)-thiocarbonate.

14. The compound according to claim 1, O-[3-Phenyl-6-chloropyridazinyl-(4)]-Q-(ethyl)-thionocarbonate.

15. The compound according to claim 1, O-[3-Phenyl-6-chloropyridazinyl-(4)]-O-(n-propyl)-thionocarbonate.

16. The compound according to claim 1, O-[3-Phenyl-6-chloropyridazinyl-(4)]-O-(n-butyl)-thionocarbonate.

17. The compound according to claim 1, O-[3-Phenyl-6-chloropyridazinyl-(4)]-O-(isobutyl)-thionocarbonate.

18. The compound according to claim 1, O-[3-Phenyl-6-bromopyridazinyl-(4)]-O-(isobutyl)-thionocarbonate.

19. The compound according to claim 1, O-[3-Phenyl-6-chloropyridazinyl-(4)]-O-(n-hexyl)-thiocarbonate.

20. The compound according to claim 1, O-[3-Phenyl-6-chloropyridazinyl-(4)]-S-(phenyl)-dithiocarbonate.

* * * * *